United States Patent [19]

Krell et al.

[11] Patent Number: 5,622,858
[45] Date of Patent: Apr. 22, 1997

[54] ARTHROBACTER STRAIN PRODUCING ESTERASE FOR THE ENANTIOSELECTIVE CLEAVAGE OF 1-ARYLALKYL ESTERS

[75] Inventors: Hans-Willi Krell, Penzberg; Peter Rasor, München, both of Germany

[73] Assignee: Boehringer Mannheim GmbH, Mannheim, Germany

[21] Appl. No.: 455,522

[22] Filed: May 31, 1995

Related U.S. Application Data

[62] Division of Ser. No. 338,499, filed as PCT/EP93/01302, May 25, 1993, abandoned.

[30] Foreign Application Priority Data

May 27, 1992 [DE] Germany ............... 42 17 506.2

[51] Int. Cl.$^6$ ................................... C12N 1/20
[52] U.S. Cl. ........................... 435/252.1; 435/830
[58] Field of Search ............................. 435/830, 876, 435/253.3, 252.1

[56] References Cited

FOREIGN PATENT DOCUMENTS 451668 10/1991 European Pat. Off. .
529085 3/1993 European Pat. Off. .

OTHER PUBLICATIONS

Cambou et al., J. Am. Chem. Soc., 1984, 106, 2687–2692.
Whitesell et al., CHIMIA, 40, 9 (Sep.), 1986.
Santaniello et al., Gazzetta Chimica Italiana, 119, 1989, 581–584.
Laumen et al., Chem. Soc. Chem. Commun., 1988, 1459–1461.
Janssen et al., Tetrahedron, vol. 47, No. 36, 7645–7662, 1991.
Mori et al., Tetrahedron, vol. 36, 91–96, 1980.
Oritani et al., Agri. Biol. Chem. 37 (8), 1923–1928, 1973.
Danda et al., Tetrahedron, 47 (41), 8701–8716, 1991.

*Primary Examiner*—Irene Marx
*Attorney, Agent, or Firm*—Nikaido, Marmelstein, Murray & Oram LLP

[57] ABSTRACT

The invention concerns a microbial esterase which enantioselectively cleaves (S)-1-phenylethyl acetate and is obtainable from Arthrobacter spec. (DSM 7034), *Pseudomonas fluorescens* (DSM 7033) or *Bacillus subtilis* (DSM 7035) as well as a process for enantioselectively cleaving a 1-arylalkyl ester of a carboxylic acid and a process for the production of an enantiomerically-pure 1-arylalkanol using this esterase.

1 Claim, 1 Drawing Sheet

I

II

III

IV

ARTHROBACTER STRAIN PRODUCING ESTERASE FOR THE ENANTIOSELECTIVE CLEAVAGE OF 1-ARYLALKYL ESTERS

This is a division of application Ser. No. 08/338,499 filed Nov. 21, 1994, now abandoned, which is a 371 of PCT/EP93/01302 filed May 25, 1993.

The invention concerns a microbial esterase which enantioselectively cleaves 1-arylalkyl esters, a process for the isolation of such a microbial esterase as well as a process for the enantioselective cleavage of 1-arylalkyl esters using such a microbial esterase.

There is a widespread use of enzymes as catalysts in large scale chemical production processes. Of particular importance in this connection is the enantioselectivity of enzymatically catalysed reactions and the property of enzymes not only to convert the natural substrates but also synthetic compounds in a corresponding manner. Enzymes can therefore also be used in the synthesis of chiral building blocks of natural substances, pharmaceutical agents, agrochemicals and fine chemicals (J. Jones, J. Sih and D. Perlmann, Applications of Biochemical Systems in Organic Chemistry, J. Wiley & Sons, New York 1976, as well as R. Prochter and S. Clark, Enzymes in Organic Synthesis, Pittman, London 1985). 1-Arylalkanols (formula I, see FIG. 1) are in this regard important synthetic building blocks for pharmaceutical agents. Numerous esterases and lipases which convert 1-arylalkyl esters and thus lead to 1-arylalkanols are known and are commercially available. However, these previously known esterases either do not cleave enantioselectively (cholesterol esterase from *Candida cylindracea* and porcine pancreas, esterases from rabbit and porcine liver, lipases from *Candida cylindracea, Geotrichum candidum, Penicillium roquefortii* and porcine pancreas) or enantioselectively cleave only the 1-arylalkyl esters of formula II (see FIG. 1; lipoprotein lipase and cholesterol esterase from *Pseudomonas spec.*, lipase from *Mucor hiemalis*, lipase from *Pseudomonas fluorescens, P. cepacia, P. spec.* and porcine pancreas; see also K. Laumen et al., J. Chem. Soc. Chem. Commun. (1988), 598–600). The enantioselectivity of a reaction is characterized by the E-value according to C. S. Chen et al. (J. Am. Chem. Soc. 104 (1982), 7294). Reactions with an E-value<20 are to be regarded as being non-enantioselective; reactions with an E-value of >50 are referred to as enantio-selective in the following. In order to produce the 1-arylalkanol of formula III (see FIG. 1) it has previously been necessary to use classical chemical methods.

The object of the present invention was therefore to provide an esterase which enantioselectively hydrolyzes 1-arylalkyl esters according to formula IV (see FIG. 1).

This object is achieved by a microbial esterase which enantioselectively cleaves (S)-1-phenylethyl acetate and is obtainable from Arthrobacter spec. (DSM 7034), *Pseudomonas fluorescens* (DSM 7033) or *Bacillus subtilis* (DSM 7035). The esterase obtainable from Arthrobacter spec. (DSM 7034) is preferred.

This enantioselective cleavage reaction is tested in this case in a known manner e.g. by means of a HPLC on a chiral column material such as e.g. cellulose-coated silica gel esterified with benzoate. Alternatively the enantiomeric purity of the product can also be determined with a polarimeter.

The esterase according to the invention has a molecular weight of ca. 100,000 D when determined by means of native polyacrylamid gel electrophoresis and exhibits an isoelectric point of ca. 4.7. This enzyme hydrolyzes substituted and unsubstituted 1-arylalkyl esters and 1-phenylalkyl esters, preferably esters of short-chained carboxylic acids (chain length 1–7 C atoms) such as the (S)-1-phenylethyl ester of acetic acid, the (S)-1-phenylpropyl ester of acetic acid or the (S)-1-(-4-methylphenyl)-ethyl ester of propionic acid. The enzyme can be stabilized by the addition of glycerol.

In order to isolate the esterase according to the invention, the aforementioned bacteria are lysed by known methods e.g. by treatment with lysozyme and benzonase in hypotonic buffer and the crude extract obtained in this manner is treated with a soluble ion exchanger, preferbly Polymin G35 (BASF, Germany). The enzyme solution obtained in this manner is purified twice by hydrophobic chromatography, preferably over phenylsepharose and finally by ion exchange chromatography, preferably on DEAE-sepharose.

Since previously only esterases have been described which enantioselectively cleave the enantiomer of 1-arylalkyl esters shown in formula II (see FIG. 1), it was surprising that an esterase was also found which converts esters of the opposite configuration (formula IV, see FIG. 1).

The invention in addition concerns a process for the isolation of a microbial esterase according to the invention which enantioselectively cleaves (S)-1-phenylethyl acetate which is characterized in that a cell lysate from Arthrobacter spec. (DSM 7034), *Pseudomonas fluorescens* (DSM 7033) or *Bacillus subtilis* (DSM 7035) is treated with a soluble ion exchanger and the esterase is isolated and purified from the solution treated in this manner by means of hydrophobic chromatography and ion-exchange chromatography.

A 10% Polymin G35 solution, pH 7.0 is for example used as the soluble ion exchanger. The hydrophobic chromatography and ion-exchange chromatography are carried out on chromatographic materials known to a person skilled in the art such as e.g. phenylsepharose for hydrophobic chromatography and DEAE-sepharose for ion-exchange chromatography. The identification of the esterase according to the invention in the eluate is preferably carried out by means of p-nitrophenylacetate cleavage and measuring the released p-nitrophenol.

The microorganisms Arthrobacter spec. DSM 7034, *Pseudomonas fluorescens* DSM 7033 and *Bacillus subtilis* DSM 7035 are also a subject matter of the invention.

The esterase according to the invention that is obtainable from these strains results in an enantioselective hydrolysis of the enantiomer of 1-arylalkyl esters shown in formula IV.

The invention additionally concerns a process for the enantioselective cleavage of a 1-arylalkyl ester of formula IV in which R1 denotes an aryl or substituted aryl residue and R2 and R3 denote an alkyl or substituted alkyl residue which is characterized in that a racemic mixture of this ester is treated with a microbial esterase according to the invention. In this case the enzyme according to the invention can be used as such or it is also possible to use a culture of microorganisms which produce this enzyme. The reaction is preferably carried out in an aqueous buffer e.g. potassium phosphate buffer at a pH value of 5–10, preferably 6–9, and at a temperature of 5° C.–50° C., preferably at 20° C.–40° C. During the reaction a base, preferably NaOH, is added by means of an autotitrator. When an adequate conversion has been achieved, preferably a 50% conversion, the reaction is terminated, preferably by an extraction that follows directly. The reaction can, however, also be terminated by lowering the pH value, by heating or by addition of an enzyme inhibitor such as PMSF (phenylmethylsulfonyl fluoride). Subsequently the enantiomerically pure 1-arylalkanol obtained is extracted with a water-immiscible organic solvent and separated from non-converted ester according to known methods by chromatography or distillation. It is expedient to determine the enantiomeric purity by means of a HPLC on a chiral column material e.g. cellulose-coated silica gel esterified with benzoate or by means of a polarimeter.

The invention in addition concerns a process for the production of a 1-arylalkanol according to formula III in which R1 denotes an aryl or substituted aryl residue and R2 denotes an alkyl or substituted alkyl residue which is characterized in that a racemic mixture of a 1-arylalkyl ester is treated with a microbial esterase according to the invention in an aqueous buffer at a pH value of 5–10, preferably 6-9 and at a temperature of 5° C.–50° C., preferably 20° C.–40° C. and subsequently the enantiomerically-pure 1-arylalkanol obtained is isolated.

Since in the enantioselective cleavage of the racemic 1-arylalkyl ester by incubation with the microbial esterase according to the invention only one enantiomer of the racemic mixture is converted, the esterase according to the invention is also suitable for purifying and isolating an enantiomerically-pure 1-arylalkyl ester according to formula II (see FIG. 1).

The microorganisms according to the invention Arthrobacter spec. DSM 7034, *Pseudomonas fluorescens* DSM 7033 and *Bacillus subtilis* DSM 7035 were deposited on Mar. 4, 1992 at the "Deutsche Sammlung für Mikroorganismen und Zellkulturen GmbH (DSM), Mascheroder Weg 1b, 3300 Braunschweig".

BRIEF DESCRIPTION OF THE DRAWING

The invention is elucidated in more detail by the following examples together with the FIGURE.

EXAMPLE 1

Figure 1:
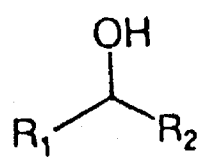
FIG. 1 shows the formulae I–IV of 1-arylalkyl esters and 1-arylalkanols in which R1 denotes an aryl or substituted aryl residue and R2 and R3 denote an alkyl or substituted alkyl residue.
Figure 1:
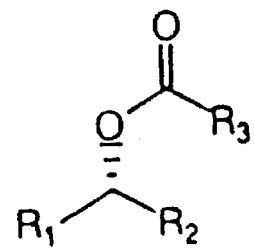
Figure 1:
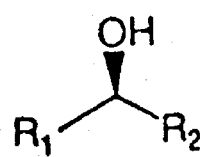
Figure 1:
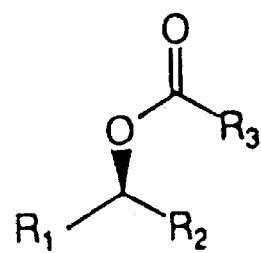

Isolation of an esterase from Arthrobacter spec. which enantioselectively cleaves (S)-1-phenylethyl acetate Arthrobacter spec. is cultured for 16 hours at 28° C. in a medium which contains 15.6 g/l special peptone (E. Merck, Germany), 2.8 g/l yeast extract (E. Merck), 5.6 g/l sodium chloride and 1 g/l glucose and has a pH value of 7.0. For cell disruption the centrifuged bacterial pellet is taken up in a 20% (w/v) suspension in 50 mmol/l potassium phosphate buffer pH 7.5 and incubated for 2 hours at 25° C. with 10 mg/ml lysozyme and 300 U/ml benzonase (E. Merck, Germany) while stirring.

80 µl of a 10% Polymin G35 solution, pH 7.0 (BASF, Germany) is added by pipette to 1 ml of the 20% crude extract obtained, it is incubated at 25° C. for 5 minutes while stirring and subsequently centrifuged for 20 minutes at 18,000 g.

The clear enzyme solution obtained after Polymin treatment is adjusted to 10 mmol/l potassium buffer pH 7.0, 10% ammonium sulfate and 0.1 mmol/l dithioerythritol (DTE). This protein sample is then applied to a phenylsepharose fast flow column (2.0×6 cm, Pharmacia, Sweden) equilibrated with 10 mmol/l potassium phosphate buffer pH 7.0, 10% ammonium sulfate and 0.1 mmol/l DTE. After washing out non-bound substances with the aforementioned equilibration buffer, bound esterase is eluted with 10 mmol/l potassium phosphate buffer pH 7.0/0.1 mmol/l DTE. The active fractions are identified by means of p-nitrophenyl acetate cleavage (according to example 2), pooled and dialyzed against 10 mmol/l potassium phosphate buffer pH 7.0/0.1 mmol/l DTE saturated with polyethylene glycol (PEG 6000) and concentrated in this process. The concentrate obtained is again applied to a phenylsepharose column which, however, in this case had been equilibrated with 100 mmol/l potassium phosphate buffer pH 7.0/0.1 mmol/l DTE. It is eluted with a gradient of 100 mmol/l to 10 mmol/l potassium phosphate buffer at a flow rate of 5 ml/min and a fraction size of 10 ml in each case. The active fractions obtained are again pooled and dialyzed against 20 mmol/l potassium phosphate buffer pH 7.5/0.1 mmol/l DTE saturated with PEG 6000 and concentrated in this process.

The concentrate obtained is finally applied to a DEAE-sepharose fast flow column (5×1.2 cm) which had been equilibrated with 20 mmol/l potassium phosphate buffer pH 7.5, 0.1 mmol/l DTE and rewashed with a 3-fold column volume.

It is eluted with a gradient of 0–0.3 mol/l sodium chloride in 20 mmol/l potassium phosphate pH 7.5/0.1 mmol/l DTE at a flow rate of 2.5 ml/min. The esterase elutes at a salt content of ca. 0.3 mol/l sodium chloride. The active fractions are pooled and dialyzed against 10 mmol/l potassium phosphate buffer pH 7.0/0.1 mmol/l DTE saturated with PEG 6000 and concentrated in this process. Glycerol is added to this solution for stabilization up to a final concentration of 60% by volume.

EXAMPLE 2

Determination of the esterase activity

1800 µl 0.2 mol/l potassium phosphate buffer pH 6.5, 100 µl p-nitrophenyl acetate (20 mmol/l in ethanol) and 100 µl of the enzyme solution to be tested are added to a cuvette with a path length of 1 cm. The measurement is carried out at 30° C. and 410 nm for 1 minute. The extinction coefficient is $15 \times 10^6$ cm$^2$/mol. One unit is defined as the amount which hydrolyzes 1 µmol p-nitrophenyl acetate in one minute under these test conditions.

EXAMPLE 3

Enzymatic resolution of racemates of 1-phenylethyl acetate

For the preparative resolution, racemic 1-phenylethyl acetate (50 mmol/l) in 10 mmol/l phosphate buffer pH 7.0 is incubated at 30° C. with the esterase according to the invention (1 unit esterase per 1 mmol ester) that was isolated according to example 1. The pH value is kept constant during the reaction by means of an automatic burette which titrates 0.1 mol/l NaOH. The reaction course is monitored by the consumption of sodium hydroxide. The enantiomeric excess of the product 1-phenylethanol as well as of the substrate 1-phenylethyl acetate is determined by HPLC on a chiral column (Chiracel OJ, Daicel Company). Once a 50% conversion is achieved, the enantiomeric excess of the retained substrate (R)-1-phenylethyl acetate is 96% and that of the product (S)-1-phenylethanol is 94% (enantioselectivity E>100). The reaction is terminated by extracting several fold with ethyl acetate. The organic phases are pooled and concentrated by evaporating the solvent. The (S)-1-phenylethanol obtained is separated from non-converted (R)-1-phenylethyl acetate by chromatography on silica gel.

We claim:

1. A biologically pure culture of Arthrobacter spec. DSM 7034.

* * * * *

UNITED STATES PATENT AND TRADEMARK OFFICE
CERTIFICATE OF CORRECTION

PATENT NO. : 5,622,858
DATED : April 22, 1997
INVENTOR(S) : KRELL et al.

It is certified that error appears in the above-indentified patent and that said Letters Patent is hereby corrected as shown below:

Title page,
Item [62], line 2 delete abandoned.

Signed and Sealed this

Thirtieth Day of September, 1997

Attest:

BRUCE LEHMAN

*Attesting Officer*    *Commissioner of Patents and Trademarks*